(12) United States Patent
Thill et al.

(10) Patent No.: US 9,833,557 B2
(45) Date of Patent: Dec. 5, 2017

(54) SYSTEMS AND METHODS FOR DETERMINING FREE PLASMA HEMOGLOBIN

(71) Applicant: Fenwal, Inc., Lake Zurich, IL (US)

(72) Inventors: Melissa A. Thill, Kenosha, WI (US); Samantha M. Planas, Wauconda, IL (US); Amit J. Patel, Algonquin, IL (US); Courtney Moore, San Diego, CA (US); William H. Cork, Mettawa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 432 days.

(21) Appl. No.: 14/577,124

(22) Filed: Dec. 19, 2014

(65) Prior Publication Data

US 2016/0175514 A1 Jun. 23, 2016

(51) Int. Cl.
*A61M 1/38* (2006.01)
*G01N 33/49* (2006.01)
(Continued)

(52) U.S. Cl.
CPC ............ *A61M 1/38* (2013.01); *A61M 1/3406* (2014.02); *A61M 1/3496* (2013.01); *G01N 21/59* (2013.01);
(Continued)

(58) Field of Classification Search
CPC ...... A61M 1/38; A61M 1/3496; G01N 33/491
See application file for complete search history.

(56) References Cited

U.S. PATENT DOCUMENTS

| 4,146,172 A | 3/1979 | Cullis et al. |
| 4,151,844 A | 5/1979 | Cullis et al. |

(Continued)

FOREIGN PATENT DOCUMENTS

| CA | 1 155 098 | 8/2011 |
| EP | 1 640 027 A1 | 3/2006 |

(Continued)

OTHER PUBLICATIONS

Extended European Search Report for EP 15 20 0464, dated May 19, 2016.

*Primary Examiner* — Toan Le
(74) *Attorney, Agent, or Firm* — Cook Alex Ltd.

(57) ABSTRACT

A system is provided for separating a plasma-containing fluid into separated plasma and a concentrated fluid. The system cooperates with a fluid flow circuit including a fluid separation chamber and a plasma outlet line associated therewith for removing separated plasma from the fluid separation chamber. The system includes an optical sensor assembly to monitor the contents of the plasma outlet line and produce an output indicative of the concentration of free plasma hemoglobin in the plasma outlet line. A controller of the system calculates the amount of free plasma hemoglobin in at least a portion of the concentrated fluid based at least in part on the output of the optical sensor assembly. The controller may periodically calibrate the optical sensor assembly by determining an instrument-specific correlation between optic output and free hemoglobin concentration and comparing it to experimentally determined data to ensure continued reliability of the optical sensor assembly.

24 Claims, 6 Drawing Sheets

(51) Int. Cl.
*A61M 1/34* (2006.01)
*G01N 21/59* (2006.01)
*A61M 1/26* (2006.01)
*A61M 1/36* (2006.01)

(52) U.S. Cl.
CPC ......... *G01N 33/491* (2013.01); *A61M 1/265* (2014.02); *A61M 1/3672* (2013.01); *A61M 2202/0415* (2013.01); *A61M 2202/0443* (2013.01); *A61M 2205/18* (2013.01); *A61M 2205/331* (2013.01); *A61M 2205/3327* (2013.01); *A61M 2205/702* (2013.01); *A61M 2205/75* (2013.01); *A61M 2230/20* (2013.01); *G01N 2201/12* (2013.01)

(56) References Cited

U.S. PATENT DOCUMENTS

| | | | |
|---|---|---|---|
| 4,185,629 A | 1/1980 | Cullis et al. | |
| 4,187,979 A | 2/1980 | Cullis et al. | |
| 4,303,336 A | 12/1981 | Cullis | |
| 4,416,654 A | 11/1983 | Schoendorfer et al. | |
| 4,464,167 A | 8/1984 | Schoendorfer et al. | |
| 4,586,190 A | 4/1986 | Tsuji | |
| 4,637,813 A | 1/1987 | DeVries | |
| 4,810,090 A | 3/1989 | Boucher et al. | |
| 4,834,890 A | 5/1989 | Brown et al. | |
| 4,952,127 A | 8/1990 | Schmeisser et al. | |
| 5,048,524 A | 9/1991 | Bailey | |
| 5,149,503 A | 9/1992 | Kohno et al. | |
| 5,194,145 A | 3/1993 | Schoendorfer | |
| 5,234,608 A | 8/1993 | Duff | |
| 5,316,667 A | 5/1994 | Brown et al. | |
| 5,348,533 A | 9/1994 | Papillon et al. | |
| 5,348,539 A | 9/1994 | Herskowitz | |
| 5,478,479 A | 12/1995 | Herrig | |
| 5,494,592 A | 2/1996 | Latham et al. | |
| 5,573,678 A | 11/1996 | Brown et al. | |
| 5,605,842 A | 2/1997 | Langley et al. | |
| 5,607,579 A | 3/1997 | Latham et al. | |
| 5,611,997 A | 3/1997 | Langley et al. | |
| 5,632,893 A | 5/1997 | Brown et al. | |
| 5,637,082 A | 6/1997 | Pages et al. | |
| 5,681,273 A | 10/1997 | Brown | |
| 5,693,232 A | 12/1997 | Brown et al. | |
| 5,704,888 A | 1/1998 | Hlavinka et al. | |
| 5,704,889 A | 1/1998 | Hlavinka et al. | |
| 5,712,798 A | 1/1998 | Langley et al. | |
| 5,730,883 A | 3/1998 | Brown | |
| 5,792,372 A | 8/1998 | Brown | |
| 5,804,079 A | 9/1998 | Brown | |
| 5,817,519 A | 10/1998 | Zelmanovic et al. | |
| 5,868,696 A | 2/1999 | Giesler et al. | |
| 5,958,250 A | 9/1999 | Brown et al. | |
| 5,961,842 A | 10/1999 | Min et al. | |
| 5,980,760 A | 11/1999 | Min et al. | |
| 6,027,657 A | 2/2000 | Min et al. | |
| 6,041,246 A | 3/2000 | Krivitski et al. | |
| 6,064,474 A | 5/2000 | Lee et al. | |
| 6,106,727 A | 8/2000 | Krasnoff et al. | |
| 6,241,649 B1 | 6/2001 | Zanella et al. | |
| 6,254,784 B1 | 7/2001 | Nayak et al. | |
| 6,262,798 B1 | 7/2001 | Shepherd et al. | |
| 6,284,142 B1 | 9/2001 | Muller | |
| 6,294,094 B1 | 9/2001 | Muller et al. | |
| 6,312,607 B1 | 11/2001 | Brown et al. | |
| 6,322,488 B1 | 11/2001 | Westberg et al. | |
| 6,348,156 B1 | 2/2002 | Vishnoi et al. | |
| 6,419,822 B2 | 7/2002 | Muller et al. | |
| 6,784,981 B1 | 8/2004 | Roche et al. | |
| 6,831,733 B2 | 12/2004 | Pettersson et al. | |
| 6,995,835 B2 | 2/2006 | Samsoondar et al. | |
| 7,400,918 B2 | 7/2008 | Parker et al. | |
| 7,463,343 B2 | 12/2008 | Muller | |
| 7,789,245 B2 | 9/2010 | Westberg et al. | |
| 8,556,793 B2 | 10/2013 | Foley et al. | |
| 2004/0223857 A1 | 11/2004 | Kline et al. | |
| 2005/0051466 A1 | 3/2005 | Carter et al. | |
| 2009/0129976 A1 | 5/2009 | Hoshino et al. | |
| 2009/0291819 A1* | 11/2009 | Westberg ............. B04B 5/0442 494/56 |
| 2011/0306856 A1 | 12/2011 | Rule et al. | |
| 2012/0178178 A1 | 7/2012 | Choi et al. | |

FOREIGN PATENT DOCUMENTS

| | | |
|---|---|---|
| JP | 2013 022021 A | 2/2013 |
| WO | WO 01/17607 A1 | 3/2001 |
| WO | WO 2012/125457 A1 | 9/2012 |
| WO | WO 2014/021917 A1 | 2/2014 |

* cited by examiner

SYSTEMS AND METHODS FOR DETERMINING FREE PLASMA HEMOGLOBIN

BACKGROUND

Field of the Disclosure

The invention relates to fluid separation systems and methods. More particularly, the invention relates to systems and methods for detecting free plasma hemoglobin in plasma separated out of a plasma-containing fluid.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., which is an affiliate of Fresenius Kabi AG of Bad Homburg, Germany, or other centrifugal separation devices, or a spinning membrane-type separator, such as the AUTOPHERESIS-C® and AURORA® devices from Fenwal, Inc.

In some of these systems, an optical device is provided for detecting the presence of free plasma hemoglobin in separated blood plasma. Known systems typically include an alert or alarm system that is programmed to generate an alert or alarm when the concentration of free plasma hemoglobin in the plasma exceeds a threshold value. However, experience has shown that the concentration of free plasma hemoglobin in the plasma varies over time, and that a high free plasma hemoglobin concentration at one instant does not necessarily indicate that an undesirable total amount of free plasma hemoglobin is being returned to a donor or patient or blood source. Accordingly, the need remains for a plasma monitoring system that can prevent the return of excess free plasma hemoglobin to a donor or patient or blood source, while eliminating or reducing the number of unnecessary or nuisance alarms or alerts caused by transient elevated free plasma hemoglobin concentration in the separated plasma.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid separation system is provided for separating a plasma-containing fluid into separated plasma and a concentrated fluid. The fluid separation system is configured to cooperate with a fluid flow circuit including a fluid separation chamber and a plasma outlet line associated with the fluid separation chamber for removing separated plasma from the fluid separation chamber. An optical sensor assembly of the system is configured to monitor the contents of the plasma outlet line and produce an output indicative of the concentration of free plasma hemoglobin in the plasma outlet line. A controller of the system is programmed to calculate the amount of free plasma hemoglobin in at least a portion of the concentrated fluid based at least in part on the output of the optical sensor assembly. A pump is configured to deliver at least a portion of the concentrated fluid to a fluid recipient, with the controller being programmed to generate an alarm or alert signal when the amount of free plasma hemoglobin in the concentrated fluid delivered to and/or to be delivered to the fluid recipient meets or exceeds a preselected or predetermined value.

In another aspect, a method is provided for calculating the amount of free plasma hemoglobin in a concentrated fluid separated from a plasma-containing fluid. The method includes separating a plasma-containing fluid into separated plasma and a concentrated fluid and optically monitoring at least a portion of the separated plasma. An output that is indicative of the concentration of free plasma hemoglobin in the separated plasma is generated, and then the amount of free plasma hemoglobin in at least a portion of the concentrated fluid is calculated based at least in part on the output. The method further includes operating a pump to deliver at least a portion of the concentrated fluid to a fluid recipient and generating an alarm or alert signal when the amount of free plasma hemoglobin in the concentrated fluid delivered to and/or to be delivered to the fluid recipient meets or exceeds a preselected or predetermined value.

In yet another aspect, a fluid separation system is provided for separating a plasma-containing fluid into separated plasma and a concentrated fluid. The fluid separation system is configured to cooperate with a fluid flow circuit including a fluid separation chamber and a plasma outlet line associated with the fluid separation chamber for removing separated plasma from the fluid separation chamber. An optical sensor assembly of the system is configured to monitor the contents of the plasma outlet line and produce an output indicative of the concentration of free plasma hemoglobin in the plasma outlet line. A controller of the system is programmed to calculate the free plasma hemoglobin concentration of the contents of the plasma outlet line based at least in part on the output of the optical sensor assembly. The controller includes a pre-programmed reference equation having one or more constants and representing an experimentally determined relationship between the output of the optical sensor assembly and free plasma hemoglobin concentration. The controller is programmed to, during a calibration test, generate an equation having one or more constants and representing the actual relationship between the output of the optical sensor assembly and free plasma hemoglobin concentration. The controller compares at least one of the constants of the pre-programmed reference equation to the corresponding constant or constants of the generated equation and registers the optical sensor assembly as having passed the calibration test if the differences between the corresponding constant or constants of the two equations are less than a predetermined tolerance away from each other. On the other hand, if the corresponding constant or constants of the two equations are greater than a predetermined tolerance away from each other, then the controller registers the optical sensor assembly as having failed the calibration test.

In another aspect, a method is provided for calibrating an optical sensor assembly configured to monitor a fluid for the presence of free plasma hemoglobin. The method includes providing at least one fluid having a known free plasma hemoglobin concentration or at least one material having optical properties that are generally representative of the optical properties of a corresponding fluid having a known free plasma hemoglobin concentration, and optically monitoring the fluid or material using the optical sensor assembly. The optical sensor assembly generates an output indicative of the concentration of free plasma hemoglobin in the fluid or corresponding fluid and then an equation is generated using the output, with the equation having one or more constants and representing the actual relationship between the output of the optical sensor assembly and the concentration of free plasma hemoglobin in the fluid or corresponding fluid. At least one of the constants of the generated equation is compared to the corresponding constant or constants of a reference equation, which represents an experimentally determined relationship between the output of the optical sensor assembly and free plasma hemoglobin concentration. The optical sensor assembly is registered as having passed the calibration test if the differences between the constant or constants of the generated equation are less than a predetermined tolerance away from the corresponding constant or constants of the reference equation, whereas the optical sensor assembly is registered as having failed the calibration test if the differences between the constant or constants of the generated equation are greater than a predetermined tolerance away from the corresponding constant or constants of the reference equation.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
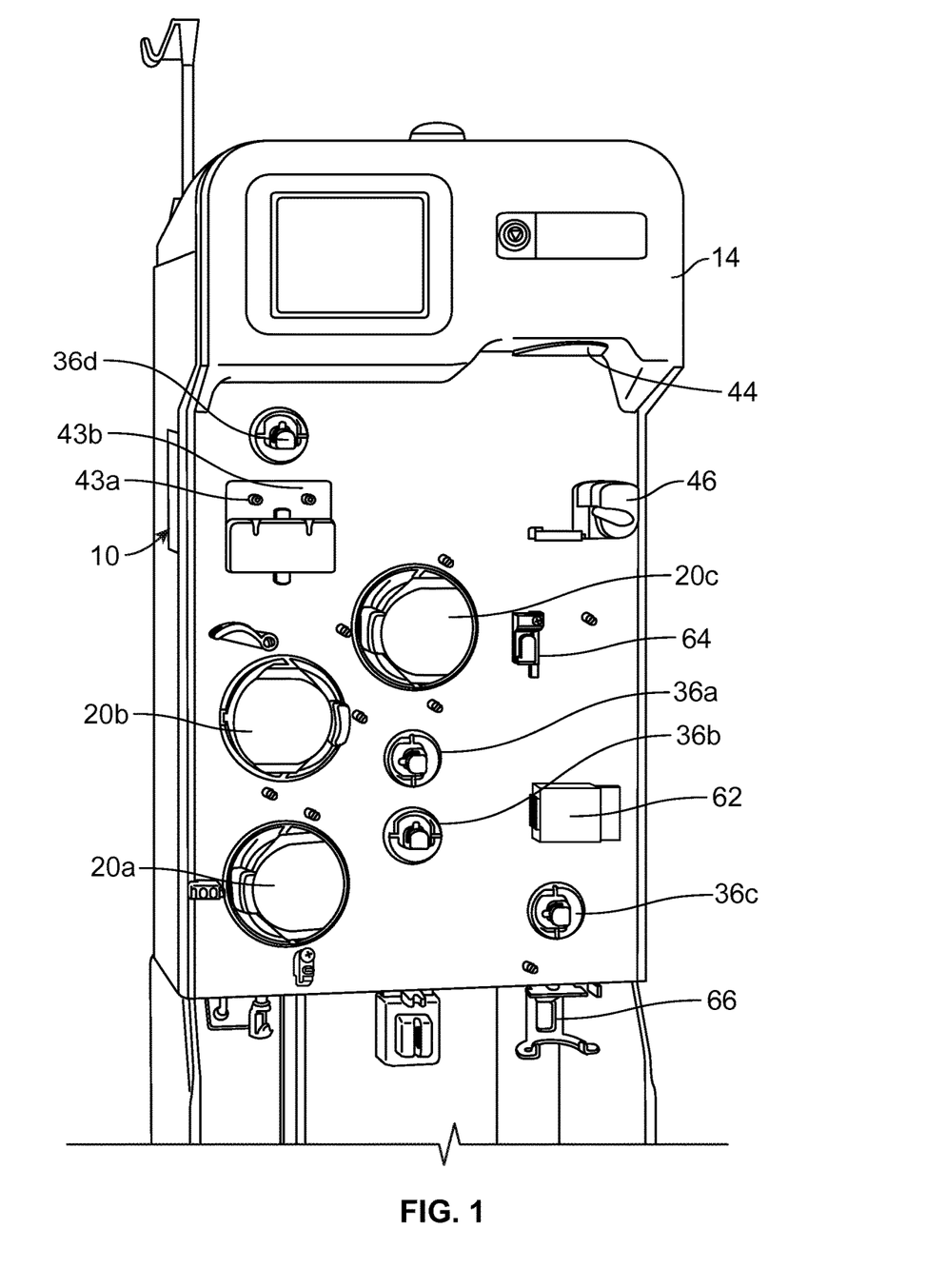
FIG. 1 is a front perspective view of an exemplary fluid separation system according to an aspect of the present disclosure.
Figure 2:
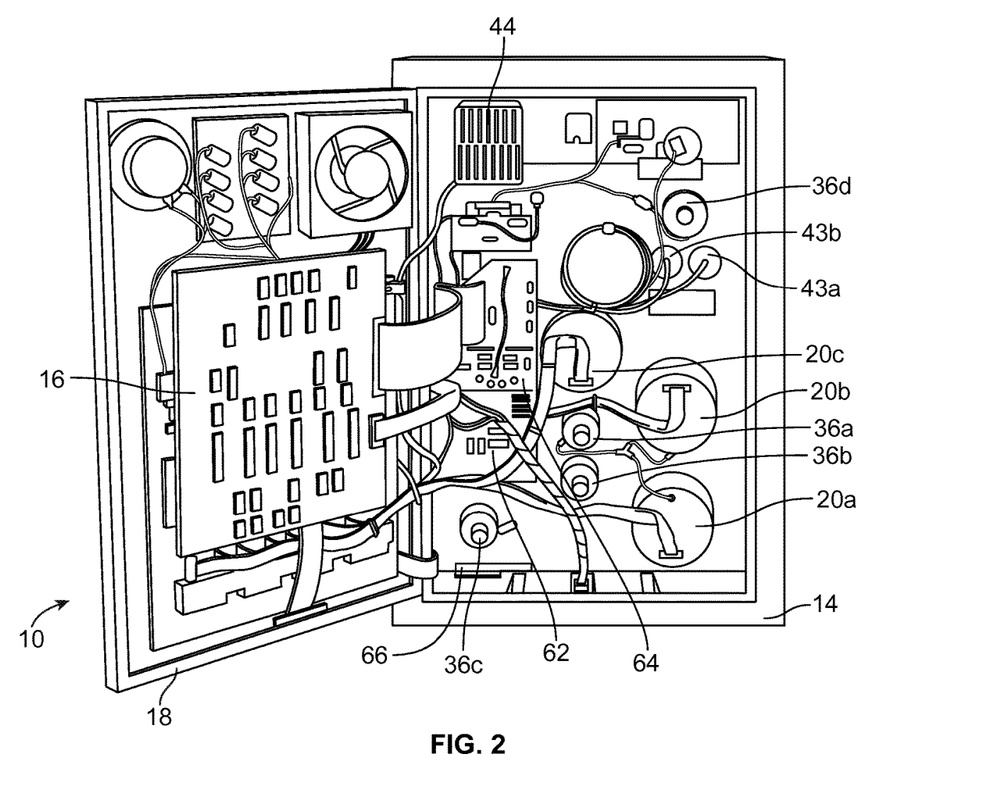
FIG. 2 is a rear perspective view of the fluid separation system of FIG. 1, with a rear door thereof in an open position.
Figure 3:
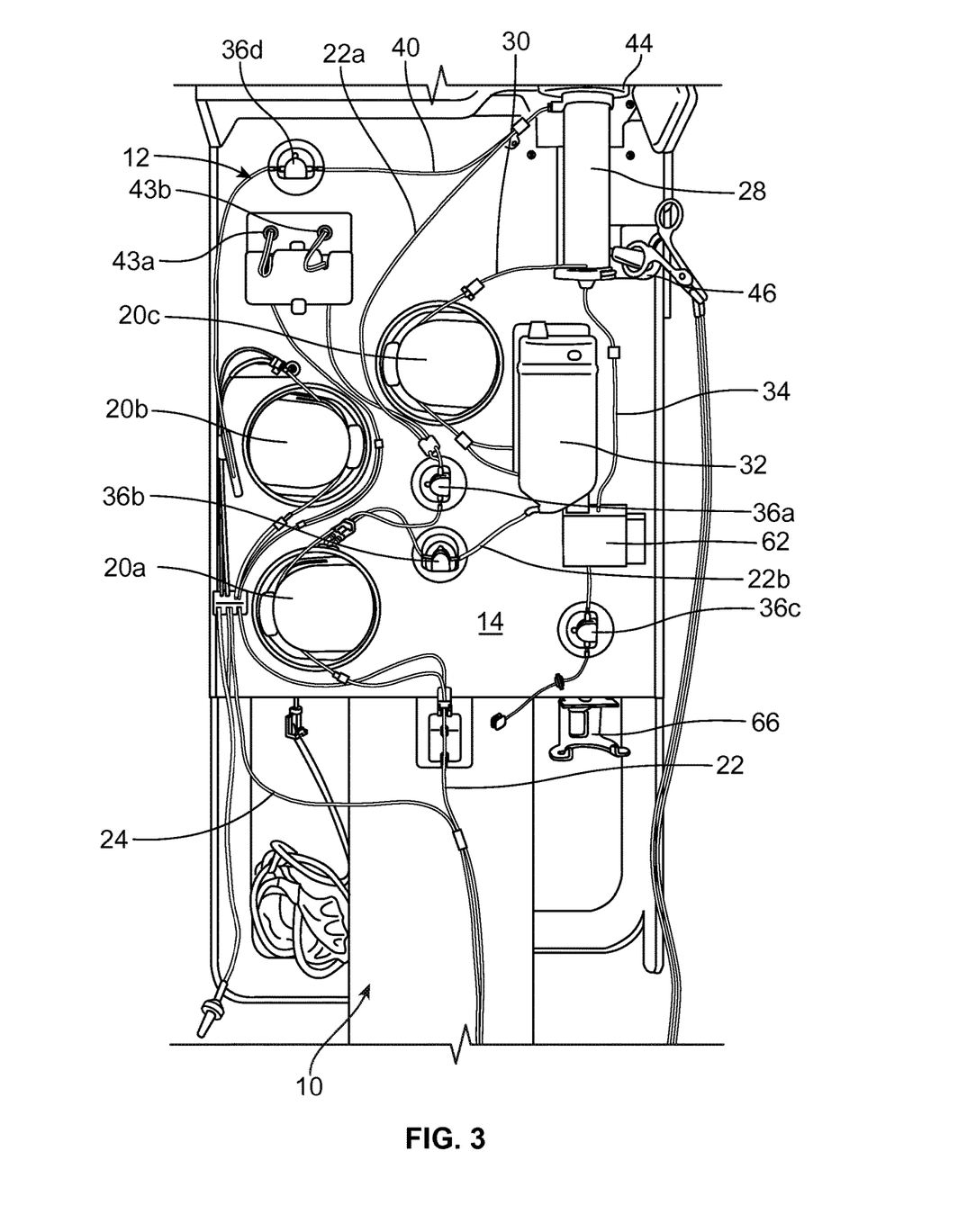
FIG. 3 is a front perspective view of the fluid separation system of FIG. 1, with a fluid flow circuit associated therewith.

According to an aspect of the present disclosure, a durable or reusable fluid separation system is used in combination with a separate fluid flow circuit (which may be disposable) to separate a plasma-containing fluid into separated plasma and a concentrated fluid. FIGS. 1 and 2 illustrate an exemplary fluid separation system 10, while FIG. 3 illustrates an exemplary fluid flow circuit 12 mounted onto the fluid separation system 10, but it should be understood that the illustrated fluid separation system 10 and fluid flow circuit 12 are merely exemplary of such systems and circuits and that differently configured fluid processing systems and fluid flow circuits may be provided without departing from the scope of the present disclosure.

The system 10 of FIG. 1 is configured for processing whole blood, but it may be used to process any other plasma-containing fluid to separate plasma from concentrated fluid (which may be red cell concentrate or packed red cells when the plasma-containing fluid constitutes whole blood). The plasma-containing fluid may come from any fluid source, which may include a living donor or patient (e.g., a human blood donor) or a non-living source (e.g., a blood bag or fluid container).

Figure 5:
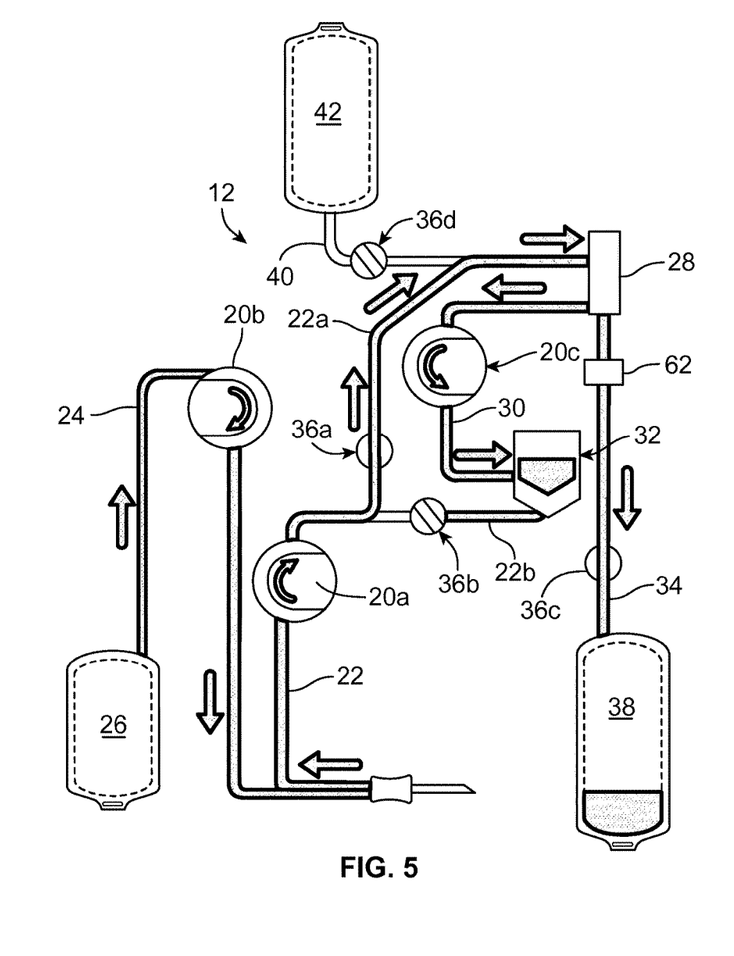
FIG. 5 is a schematic view of the fluid flow circuit and fluid separation system of FIG. 3, in a fluid draw mode.
Figure 6:
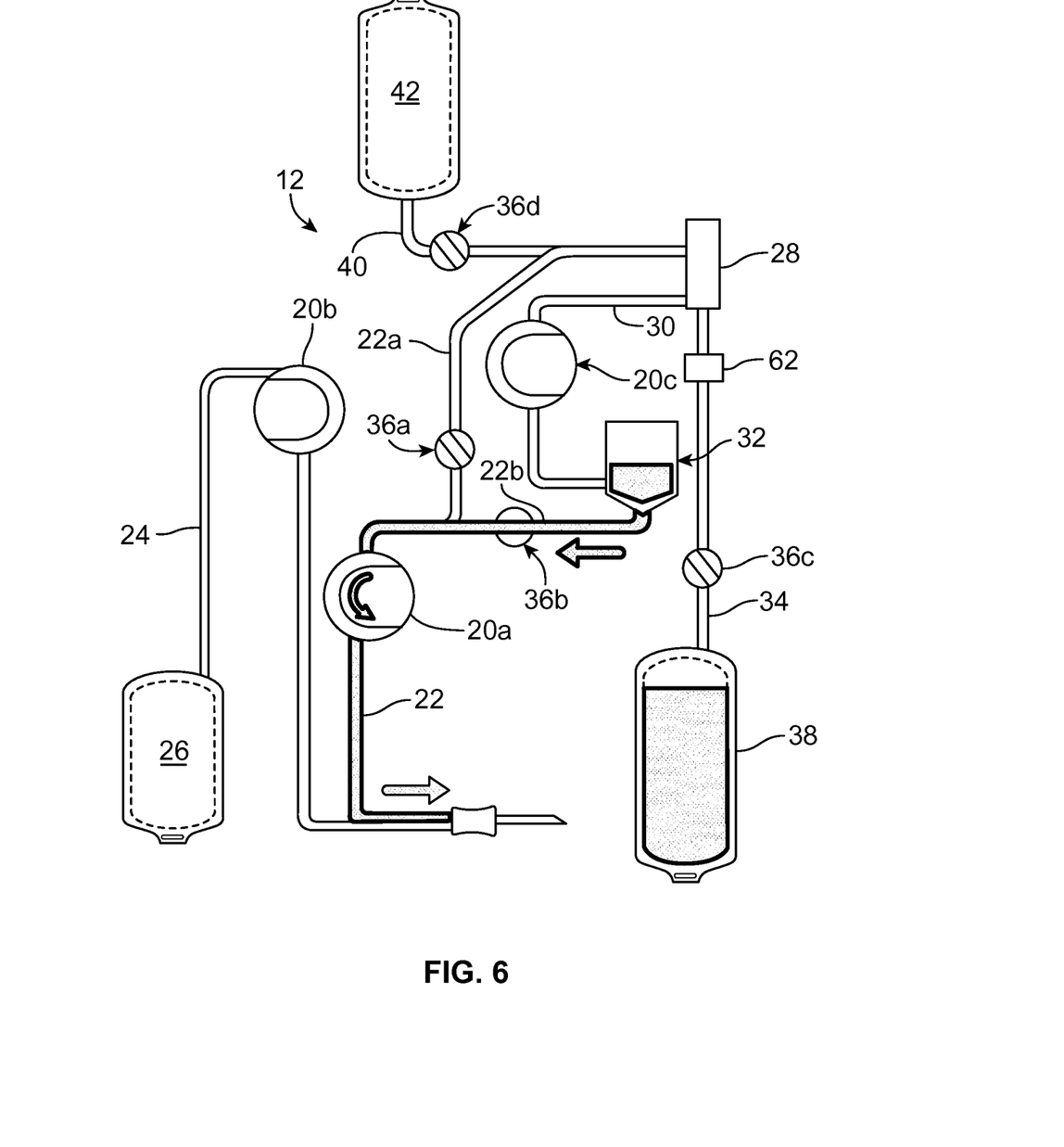
FIG. 6 is a schematic view of the fluid flow circuit and fluid separation system of FIG. 3, in a fluid return mode.

The illustrated system 10 includes a cabinet or housing 14, with several components positioned outside of the cabinet 14 (e.g., associated with a front wall or surface or panel of the cabinet 14) and additional components (including a central processing unit or controller 16) and interconnects positioned inside of the cabinet 14, which may be accessed by opening a rear door 18 of the system 10, as shown in FIG. 2. It should be understood that the illustrated system components and the location of the components is merely exemplary, and that additional or different components and different component arrangements may be incorporated into the system without departing from the scope of the present disclosure. Among the system components positioned on the outside of the cabinet 14, one or more pumps or pump stations 20a-20c may be provided, with the pumps 20a-20c configured to accommodate tubing lines of the fluid flow circuit 12. One of the pumps 20a may be provided as a source/recipient access pump, which may be associated with a source/recipient access line 22 of the fluid flow circuit 12 and operates to draw fluid from a fluid source (FIG. 5) and to return fluid to a fluid recipient (FIG. 6). Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. A third pump 20c may be provided as a concentrated fluid pump, which may be associated with a concentrated fluid outlet line 30 and operates to draw concentrated fluid from the fluid separation chamber 28 and direct it into a concentrated fluid reservoir 32 after the plasma-containing fluid has been separated into a concentrated fluid and separated plasma in the fluid separation chamber 28.

In the illustrated embodiment, the pumps 20a-20c are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a plasma outlet line 34 of the fluid flow circuit 12 to draw separated plasma from the fluid separation chamber 28 after the plasma-containing fluid has been separated into a concentrated fluid and separated plasma. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a concentrated fluid reservoir 32 of the fluid flow circuit 12 to allow (FIG. 6) or prevent (FIG. 5) the flow of concentrated fluid through the reinfusion branch 22b. A third clamp or valve 36c may be provided as a plasma clamp or valve, which may be associated with the plasma outlet line 34 to allow (FIG. 5) or prevent (FIG. 6) the flow of separated plasma through the plasma outlet line 34 and into a separated plasma container 38. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure.

The system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the fluid separation chamber 28 may include a tubular housing 48 (FIG. 4), with a microporous membrane 50 positioned therein. An inlet 52 allows a plasma-containing fluid to enter into the housing 48 (via the draw branch 22a of the source/recipient access line 22), while a side outlet 54 allows concentrated fluid to exit the housing 48 (via the concentrated fluid outlet line 30) and a bottom outlet 56 allows separated plasma to exit the housing 48 (via the plasma outlet line 34) after the plasma-containing fluid has been separated into concentrated fluid and plasma.

Figure 4:
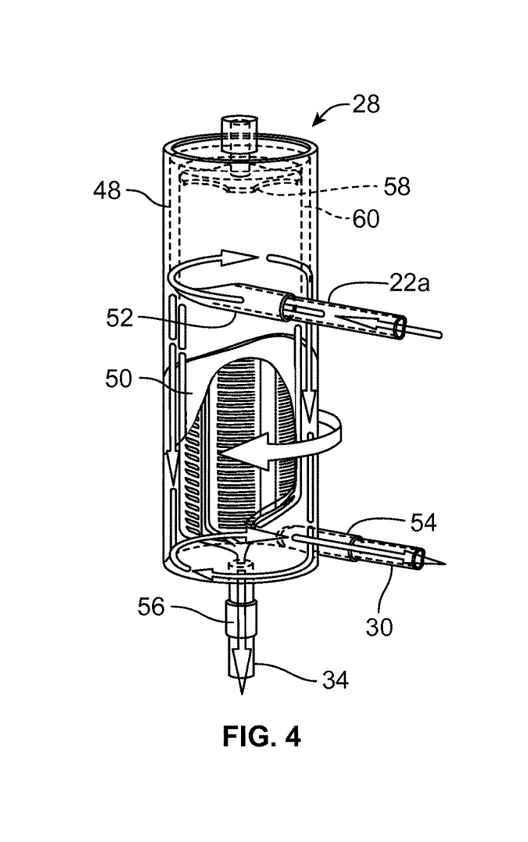
FIG. 4 is a front perspective view of a fluid separation chamber of the fluid flow circuit of FIG. 3, with a portion thereof broken away for illustrative purposes.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the concentrated fluid (which may be cellular blood components) away from the membrane 50 to exit the fluid separation chamber 28 via the side outlet 54, while the separated plasma passes through the membrane 50 toward the central axis of the housing 48 to exit the fluid separation chamber 28 via the bottom outlet 56. It should be understood that the present disclosure is not limited to a particular fluid separation chamber and that the illustrated and described fluid separation chamber 28 is merely exemplary. For example, in other embodiments, a centrifugal device that separates fluid components based on density, rather than size, may be employed to separate a plasma-containing fluid into plasma and a concentrated fluid.

The system 10 further includes a hemoglobin detector or optical sensor assembly 62 associated with the plasma outlet line 34 when the fluid flow circuit 12 has been installed on the system 10. The optical sensor assembly 62 is used to determine the concentration of free plasma hemoglobin in the separated plasma flowing through the plasma outlet line 34 (and may also detect other irregularities in the plasma outlet line 34, such as red blood cells, lipids, and air bubbles) and may be variously configured. In one embodiment, the optical sensor assembly 62 includes a red light source and a green light source, which may be provided as light-emitting diodes. The optical sensor assembly 62 may also include at least one light detector or sensor that is configured and oriented to receive light from one or both of the light sources. The optical sensor assembly 62 may include a cover or housing that blocks ambient light from reaching the detector(s) and/or one or more mirrors or reflective elements that maximize the light from the light sources that reaches the detector(s).

Separated plasma passing through the plasma outlet line 34 is relatively clear and uncolored in the absence of free plasma hemoglobin, such that substantially all of the light emitted into the plasma outlet line 34 should exit the plasma outlet line 34 and be received by the detector(s). Any loss of light caused by the presence of the tubing itself may be taken into account to isolate the effect of the plasma in the tubing when light passes therethrough. If the plasma outlet line 34 contains an optically dense, but colorless fluid, then the transmissivity of both red and green light through the plasma outlet line 34 will decrease to similar degrees. This is most likely to occur if the plasma is highly lipemic, but may also occur when an air bubble is present in the separated plasma or if the plasma outlet line 34 is improperly aligned within the optical sensor assembly 62. If free plasma hemoglobin is present in the separated plasma, then the transmissivity of green light through the plasma outlet line 34 will decrease to a greater extent than the decrease in the transmissivity of red light through the plasma outlet line 34. The difference between the transmission of green and red light through the plasma outlet line 34 is indicative of the concentration of free plasma hemoglobin in the separated plasma present in the portion of the plasma outlet line 34 positioned within the optical sensor assembly 62 during the time period over which a reading is taken. An exemplary system using red and green light to detect the presence of free plasma hemoglobin in separated plasma and determining its concentration is described in greater detail in U.S. Pat. No. 7,789,245, which is hereby incorporated herein by reference. It should be understood that this is only one system for detecting the presence of free plasma hemoglobin in separated plasma and determining its concentration and that any other suitable system and method for determining the concentration of free plasma hemoglobin in separated plasma may be employed without departing from the scope of the present disclosure The controller 16 may match up the relative absorbance of red and green light to a corresponding free plasma hemoglobin concentration from a chart, index, or array of values stored within the controller 16 or an associated data location or calculate the free plasma hemoglobin concentration using a mathematical formula that relates relative absorbance of red and green light to free plasma hemoglobin concentration. The correlation between relative absorbance of red and green light and free plasma hemoglobin concentration may be experimentally determined by measuring the absorbance of red and green light for a plurality of fluids having different, known free plasma hemoglobin concentrations. A relationship between relative absorbance of red and green light and free plasma hemoglobin concentration may then be derived from the experimentally observed values, which relationship may be incorporated into the aforementioned chart, index, or array of values or mathematical formula that is used by the controller 16 to determine free plasma hemoglobin concentration from an absorbance value.

According to one approach, experimental data is gathered to establish a relationship between red and green light absorbance and free plasma hemoglobin concentration. To the extent that the performance of each individual optical sensor assembly unit may vary due to any of a number of factors (e.g., a minute variation in the brightness of the red and/or green light sources), this data may be gathered by the manufacturer of the optical sensor assembly 62 using a plurality of different units to arrive at reference values that are not unduly influenced by the particular characteristics of any single unit. The data may be represented by a two-dimensional plot (e.g., with free plasma hemoglobin concentration on its x-axis and some measure of light absorbance on its y-axis), which plot may be expressed as an equation or algorithm. Depending on the nature of the data, it may be expressed by any of a variety of equations, such as a linear equation, a quadratic equation, a cubic equation, and/or a logarithmic equation. One of these equations may be selected as the "reference equation," which the controller 16 uses to gauge the accuracy of individual optical sensor assembly units.

To calibrate the optical sensor assembly 62, two or more fluids having different, known free plasma hemoglobin concentration levels may be tested by the optical sensor assembly 62 to determine a measured free plasma hemoglobin concentration for each fluid. Alternatively, rather than using fluids having known hemoglobin concentration levels, it is also within the scope of the present disclosure for the optical sensor assembly 62 to be calibrated using two or more materials having optical properties (when analyzed by the optical sensor assembly 62) that are sufficiently or generally representative or indicative of the optical properties of fluids having different, known hemoglobin concentration levels or generally similar or comparable to or (more preferably) substantially the same as or identical to the optical properties of corresponding fluids having different, known hemoglobin concentration levels. The known free plasma hemoglobin concentrations and respective optical outputs of the optical sensor assembly 62 are used to generate an equation that corresponds to the reference equation (e.g., if the reference equation is a cubic equation, then a cubic equation is generated using the measured free plasma hemoglobin concentrations). The equation generated using the measured free plasma hemoglobin concentrations is compared to the reference equation to determine whether the optical sensor assembly 62 is working properly. For example, in one embodiment one or more of (but preferably all of) the constants or coefficients or parameters of the equation generated using the measured free plasma hemoglobin concentrations are compared to the corresponding constants or coefficients or parameters of the reference equation to quantify the difference therebetween (e.g., the difference in the y-intercept of the two equations). If the constants or coefficients or parameters of the equation generated using the measured free plasma hemoglobin concentrations are within a predetermined tolerance, then the optical sensor assembly 62 will be considered to have passed the test and may be used to measure free plasma hemoglobin concentrations. On the other hand, if the variance of one or more of the constants or coefficients or parameters of the equation generated using the measured free plasma hemoglobin concentrations from the corresponding constant(s) or coefficient(s) or parameter(s) of the reference equation is greater than a certain tolerance, then the optical sensor assembly 62 will be considered to have failed the test and will have to be recalibrated or otherwise serviced to bring its operation closer in line with the established performance. This testing procedure may be carried out periodically (e.g., annually) to ensure that the performance of the optical sensor assembly 62 has not degraded to the point that it requires servicing.

The number of fluids tested by the optical sensor assembly 62 during the above testing procedure may vary without departing from the scope of the present disclosure. For example, if the reference equation is a linear equation, then it may be sufficient to test only two fluids, whereas it may be necessary to test a greater number of fluids if the reference equation is a higher order equation (e.g., a cubic or quadratic equation). It may be advantageous to select fluids having very different free plasma hemoglobin concentrations for a more accurate representation of the performance of the optical sensor assembly 62 over the full range of concentrations that it may be required to analyze. According to one approach a fluid having a relatively low free plasma hemoglobin concentration (e.g., 0-20 mg/dL) and a fluid having a relatively high free plasma hemoglobin concentration (e.g., 170-200 mg/dL) are selected as minimum and maximum values to be tested. If appropriate, fluids having free plasma hemoglobin concentrations between the two extreme values may also be tested for a more accurate representation of the performance of the optical sensor assembly 62. If it is observed that the relationship between relative absorbance of red and green light and free plasma hemoglobin concentration breaks down above a certain free plasma hemoglobin concentration level (e.g., above 200 mg/dL), then such the concentration of the fluid having the greatest known concentration may be equal to that level. During use, the controller 16 may be programmed to generate an alert or alarm signal at or above such an elevated free plasma hemoglobin concentration to notify an operator that the free plasma hemoglobin concentration may not be accurately determined. If the free hemoglobin concentration is at such an elevated level, it may be an indication that the system 10 is not operating properly or at an acceptable efficiency level.

Other approaches to translating absorbance to free plasma hemoglobin concentration and ensuring continued accuracy of the optical sensor assembly 62 may also be employed by the controller 16 without departing from the scope of the present disclosure.

According to one method of using the fluid separation system 10 and fluid flow circuit 12, a plasma-containing fluid is drawn from a fluid source into the fluid separation chamber 28 during a draw phase or mode (FIG. 5), where it is separated into concentrated fluid and separated plasma. The separated plasma is retained by the system 10, while the concentrated fluid is returned to a fluid recipient during a return or reinfusion phase or mode (FIG. 6). In one embodiment, the draw and return phases are repeatedly alternated (drawing from the fluid source, separating the fluid into plasma and concentrated fluid, and then returning the concentrated fluid to the fluid recipient) until a target (e.g., a collected amount of separated plasma) is achieved. All of the draw phases and all of the return phases may be identical or may differ from each other. For example, a final draw phase may draw less fluid from the fluid source than the previous draw phases and a final return phase may infuse a combination of concentrated fluid and replacement fluid to the fluid recipient, whereas the previous return phases return only concentrated fluid to the fluid recipient.

Figure 7:
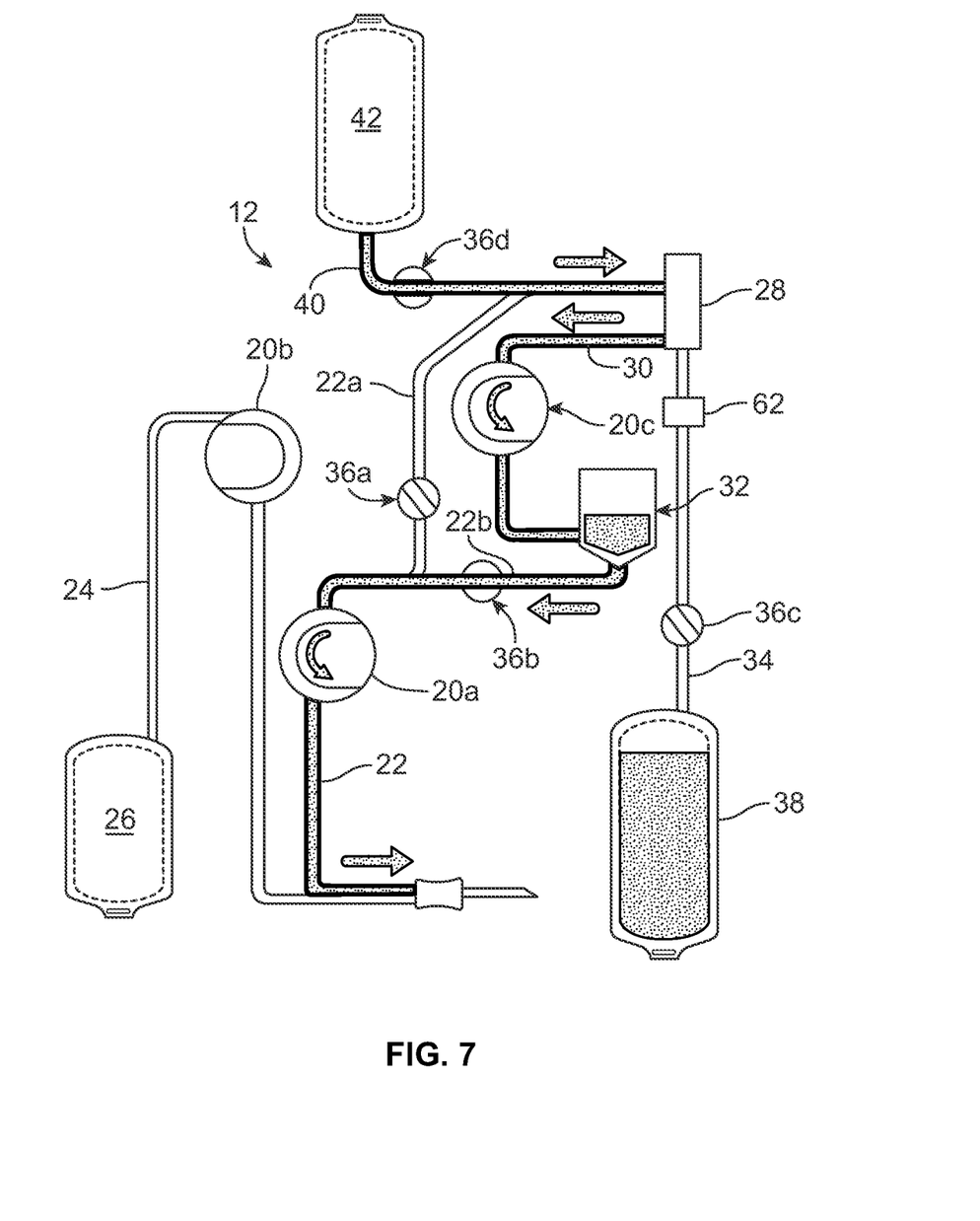
FIG. 7 is a schematic view of the fluid flow circuit and fluid processing system of FIG. 3, in a replacement fluid return mode.

FIG. 7 shows an exemplary phase or mode in which replacement fluid (e.g., saline) is directed to the fluid recipient, either alone or with an amount of concentrated fluid. In the phase of FIG. 7, the clamp or valve 36d associated with the replacement fluid line 40 is opened to allow replacement fluid to flow out of the replacement fluid source 42. The clamp or valve 36a associated with the draw branch 22a of the source/recipient access line 22 may be in a closed condition to prevent fluid flow therethrough, such that the replacement fluid is directed into the fluid separation chamber 28. The replacement fluid is pulled out of the fluid separation chamber 28 and into the concentrated fluid reservoir 32 by operation of the pump 20c associated with the concentrated fluid outlet line 30. If there is any concentrated fluid in the concentrated fluid reservoir 32, then the replacement fluid mixes with the concentrated fluid prior to being pumped to the fluid recipient by the pump 20a associated with the source/recipient access line 22, otherwise the replacement fluid alone may be pumped to the fluid recipient. In one embodiment, the replacement fluid return mode of FIG. 7 is carried out only once, as a final return phase (e.g., when the amount of concentrated fluid in the concentrated fluid reservoir 32 is at a sufficiently low level) in which a mixture of concentrated fluid and replacement fluid is returned to the fluid recipient. This may be advantageous to ensure that all of the concentrated fluid in the concentrated fluid reservoir 32 (along with any remaining in the fluid separation chamber 28) is rinsed out of the concentrated fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the fluid separation chamber 28 and the concentrated fluid reservoir 32 if the replacement fluid is being pumped to a fluid recipient earlier in the procedure. In this case, the clamp or valve 36d associated with the replacement fluid line 40 and the clamp or valve 36a associated with the draw branch 22a of the source/recipient access line 22 may be opened to allow fluid flow therethrough, with the clamp or valve 36b associated with the reinfusion branch 22b in a closed condition to prevent fluid flow therethrough. The pump 20a associated with the source/recipient access line 22 may be activated (with the other two pumps 20b and 20c inactive) to draw replacement fluid out of the replacement fluid source 42 and through the replacement fluid line 40, the draw branch 22a, and finally the source/recipient access line 22 to the fluid recipient.

A number of maladies are known to arise from the infusion of excess levels of free plasma hemoglobin to a fluid recipient, such that it would be advantageous to determine the total amount of free plasma hemoglobin in the concentrated fluid (which hemoglobin would be present in plasma of the concentrated fluid). If the amount of free plasma hemoglobin in the plasma of the concentrated fluid is known, then it may be compared to a predetermined or preselected value, with the controller 16 generating an alert or alarm signal if the total amount of free plasma hemoglobin in the plasma of the concentrated fluid equals or exceeds such value. The controller 16 may also consider the amount of free plasma hemoglobin that has already been returned to the fluid recipient during earlier return phases, how much free plasma hemoglobin has been generated but not yet returned, and/or the total amount of free hemoglobin that may be safely returned to the fluid recipient. According to an aspect of the present disclosure, the controller may use the free plasma hemoglobin concentration of the separated plasma to determine the amount of free plasma hemoglobin in the concentrated fluid. This may be achieved in any of a number of ways, which will be described below in greater detail.

According to a first approach, the controller 16 multiplies the free plasma hemoglobin concentration of the separated plasma in the plasma outlet line 34 by a ratio factor to estimate the concentration of free plasma hemoglobin in the plasma of the concentrated fluid. The ratio factor may be determined experimentally and may vary from system to system, as well as between different separation routines carried out by a single system. In one embodiment, the ratio factor may be derived by measuring the concentration of free plasma hemoglobin in the plasma of the concentrated fluid at one or more different times during a procedure. The measured concentration may then be compared to the concentration of free plasma hemoglobin in the separated plasma at the same times during the procedure to determine the ratio between the concentration of free plasma hemoglobin in the two substances (i.e., separated plasma and concentrated fluid) at the one or more different times. Depending on the experimental results, it may be appropriate to use the same ratio factor at any time during the procedure, but it is also within the scope of the present disclosure for different ratio factors to be used at different times during the procedure, if the experimental data shows a varying ratio at different points of the procedure. In one embodiment, the ratio factor is in the range of 0 to 10, which means that the free plasma hemoglobin concentration of the plasma of the concentrated fluid may be less than the free plasma hemoglobin concentration of the separation plasma (if the ratio factor is less than one) or up to ten times as great as the free plasma hemoglobin concentration of the separated plasma (based on experimental results). As the free plasma hemoglobin concentration of the separated plasma and the plasma of the concentrated fluid may vary throughout the course of a separation procedure, it may be advantageous for the controller to periodically determine the hemoglobin concentration of the separated plasma for consecutive portions of the separated plasma as it passes through the plasma outlet line 34, with each reading being multiplied by the ratio factor to arrive at the free plasma hemoglobin concentration of a corresponding portion of the plasma of the concentrated fluid.

The controller 16 may then multiply the free plasma hemoglobin concentration of the plasma of the concentrated fluid by the amount of plasma in the concentrated fluid to arrive at the total amount of free plasma hemoglobin in the plasma of the concentrated fluid. The amount of plasma in the concentrated fluid may be determined by any suitable approach without departing from the scope of the present disclosure. According to one approach, the amount of plasma in the concentrated fluid may be calculated by determining the volume of the concentrated fluid and multiplying by the percentage of that volume which is attributable to the plasma of the concentrated fluid. The volume of the concentrated fluid may be determined by any suitable approach, such as by the controller 16 multiplying the volumetric flow rate of the concentrated fluid pump 20c by the length of time that the concentrated fluid pump 20c is operated or by reference to the density and weight (which may be determined using a concentrated fluid weigh scale 64 associated with the concentrated fluid reservoir 32) of the concentrated fluid. The percentage of the volume of the concentrated fluid that is attributable to the plasma (which is related to the hematocrit of the concentrated fluid, if the plasma-containing fluid is blood) may be determined by any suitable approach, including estimation based on experimental data or optical monitoring of the concentrated fluid passing through the concentrated fluid outlet line 30.

As the free plasma hemoglobin concentration of the plasma of the concentrated fluid may vary throughout the course of a separation procedure, it may be advantageous for the controller 16 to periodically determine the amount of free plasma hemoglobin in consecutive portions of the plasma of the concentrated fluid (e.g., once for each monitoring cycle of the separated plasma) and then add the incremental amounts together to arrive at the total amount of free plasma hemoglobin in the plasma of the concentrated fluid.

According to another approach (which may be carried out instead of the first approach or in combination with the first approach), the free plasma hemoglobin concentration of the separated plasma is first used by the controller 16 to calculate the amount of free plasma hemoglobin in the separated plasma. The controller 16 may calculate the amount of free plasma hemoglobin in the separated plasma by any suitable approach, such as by multiplying the free plasma hemoglobin concentration of the separated plasma by the volume of separated plasma. The volume of the separated plasma may be determined by any suitable approach, such as by the controller calculating the volumetric flow rate of the separated plasma through the plasma outlet line 34 (e.g., by subtracting the volumetric flow rate of the concentrated fluid pump 20c from the volumetric flow rate of the source/recipient access pump 20a) and multiplying it by the length of time that the source/recipient access pump 20a and concentrated fluid pump 20c are operated or by reference to the density and weight (which may be determined using a plasma weigh scale 66 associated with the separated plasma container 38) of the separated plasma. As the free plasma hemoglobin concentration of the separated plasma may vary throughout the course of a separation procedure, it may be advantageous for the controller 16 to periodically determine the free plasma hemoglobin concentration and content of the separated plasma for consecutive portions of the separated plasma as it passes through the plasma outlet line 34, with the incremental amounts of free plasma hemoglobin being added together by the controller 16 to arrive at the total amount of free plasma hemoglobin in the separated plasma.

The concentration or amount of free plasma hemoglobin in the separated plasma may itself be useful information, apart from its use in determining the amount of free plasma hemoglobin in the plasma of the concentrated fluid, so the value calculated by the controller 16 may be separately retained and/or analyzed. For example, if the separated plasma is to be stored for later infusion to a fluid recipient, the amount of free plasma hemoglobin therein and/or the free plasma hemoglobin concentration of the stored plasma may be associated with the separated plasma container 38 (e.g., by printing the free plasma hemoglobin content and/or concentration on a label affixed to the separated plasma container 38 after the separation procedure has been completed) to ensure that an excess amount of free plasma hemoglobin is not given to the fluid recipient. Alternatively, if the separated plasma is to be processed by fractionation or the like, similar labeling of the free plasma hemoglobin content and/or concentration of the separated plasma may be useful in determining if the separated plasma is usable for the fractionation/processing procedure.

The controller 16 may then multiply the amount of free plasma hemoglobin in the separated plasma in the plasma outlet line 34 by a ratio factor to arrive at the amount of free plasma hemoglobin in the plasma of the concentrated fluid. The ratio factor may be determined experimentally and may vary from system to system, as well as between different separation routines carried out by a single system. In one embodiment, the ratio factor is in the range of 0 to 10, which means that the amount of free plasma hemoglobin in the plasma of a portion of the concentrated fluid may be less than the amount of free plasma hemoglobin in the corresponding portion of the separated plasma (if the ratio factor is less than one) or up to ten times as great as the amount of free plasma hemoglobin in the corresponding portion of the separated plasma (based on experimental results).

When the controller 16 has determined the total amount of free plasma hemoglobin in the plasma of the concentrated fluid (e.g., using either or both of the above approaches), it may compare the amount to a predetermined or preselected value to ensure that the total amount of free plasma hemoglobin to be returned to the fluid recipient does not meet or exceed the amount that may be safely returned to the fluid recipient. The predetermined or preselected value may be a single value that is used for all fluid recipients or may be a value that is based upon the nature of the individual fluid recipient (e.g., the value may be based on the weight or blood volume of the fluid recipient, in the case of a living fluid recipient). As described above, if the system 10 operates on a batch system, rather than continuously returning concentrated fluid to the fluid recipient or returning all of the concentrated fluid to the fluid recipient at one time, then the controller 16 may consider the amount of free plasma hemoglobin previously returned to the fluid recipient during earlier return phases when determining whether the amount of free plasma hemoglobin in the concentrated fluid reservoir 32 exceeds the predetermined or preselected value.

If the controller 16 determines that the total amount of free plasma hemoglobin in the plasma of the concentrated fluid meets or exceeds the predetermined or preselected value, it may react in any of a number of ways. For example, the controller 16 may trigger an alarm or alert condition to notify the operator that all of the concentrated fluid may not be directed to the fluid recipient without meeting or exceeding the predetermined or preselected value. The controller 16 may then prevent any further return of concentrated fluid to the fluid recipient or allow only a portion of the concentrated fluid to be returned to the fluid recipient. In one embodiment, the controller 16 may prompt the operator to indicate whether to return any additional concentrated fluid to the fluid recipient or not, while in another embodiment the controller 16 may automatically determine whether to return any additional concentrated fluid to the fluid recipient or not. It is also within the scope of the present disclosure for the controller 16 to carry out any other routine or response upon determining that the amount of free plasma hemoglobin in the plasma of the concentrated fluid meets or exceeds the predetermined or preselected value.

Temporary increases in levels of free plasma hemoglobin concentrations that would cause an alarm or alert condition in known systems may not cause an alarm or alert to be triggered when a system and/or method according to the present disclosure is employed. A single alarm in the event that the total free plasma hemoglobin to be returned to a fluid recipient meets or exceeds a predetermined or preselected level thus provides a sufficient safeguard against over-infusion of free plasma hemoglobin while eliminating nuisance alarms.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid separation system for separating a plasma-containing fluid into separated plasma and a concentrated fluid, the fluid separation system being configured to cooperate with a fluid flow circuit including a fluid separation chamber and a plasma outlet line associated with the fluid separation chamber for removing separated plasma from the fluid separation chamber, the fluid separation system comprising:
an optical sensor assembly configured to monitor the contents of the plasma outlet line and produce an output indicative of the concentration of free plasma hemoglobin in the plasma outlet line;
a controller programmed to calculate the amount of free plasma hemoglobin in at least a portion of the concentrated fluid based at least in part on the output of the optical sensor assembly; and
a pump configured to deliver at least a portion of the concentrated fluid to a fluid recipient, wherein the controller is programmed to generate an alarm or alert signal when the amount of free plasma hemoglobin in the concentrated fluid delivered to and/or to be delivered to the fluid recipient meets or exceeds a preselected or predetermined value.

2. The fluid separation system of claim 1, wherein the controller is programmed to determine the amount of separated plasma passing through the plasma outlet line during a period of time based at least in part on a pump rate of the pump during said period of time and to calculate the amount of free plasma hemoglobin passing through the plasma outlet line during said period of time by multiplying the concentration of free plasma hemoglobin in the plasma outlet line by the amount of separated plasma passing through the plasma outlet line during said period of time.

3. The fluid separation system of claim 2, wherein the controller is programmed to calculate the total amount of free plasma hemoglobin that has passed through the plasma outlet line by calculating the amount of free plasma hemoglobin passing through the plasma outlet line during a plurality of consecutive periods of time and adding together said amounts of free plasma hemoglobin passing through the plasma outlet line during said plurality of consecutive periods of time.

4. The fluid separation system of claim 1, further comprising a plasma weigh scale, wherein the controller is programmed to determine the amount of separated plasma that has passed through the plasma outlet line during a period of time based at least in part on a change of weight registered by the plasma weigh scale during said period of time and to calculate the amount of free plasma hemoglobin that has passed through the plasma outlet line during said period of time by multiplying the concentration of free plasma hemoglobin in the plasma outlet line by the amount of plasma that has passed through the plasma outlet line during said period of time.

5. The fluid separation system of claim 4, wherein the controller is programmed to calculate the total amount of free plasma hemoglobin that has passed through the plasma outlet line by calculating the amount of free plasma hemoglobin that has passed through the plasma outlet line during a plurality of consecutive periods of time and adding together said amounts of free plasma hemoglobin that have passed through the plasma outlet line during said plurality of consecutive periods of time.

6. The fluid separation system of claim 1, wherein the controller is programmed to calculate the amount of free plasma hemoglobin in said at least a portion of the concentrated fluid by calculating the amount of free plasma hemoglobin in the separated plasma and multiplying said amount of free plasma hemoglobin in the separated plasma by a ratio factor.

7. The fluid separation system of claim 1, wherein the controller is programmed to calculate the amount of free plasma hemoglobin in said at least a portion of the concentrated fluid by multiplying the concentration of free plasma hemoglobin in the plasma outlet line by a ratio factor and by either the amount of plasma in said at least a portion of the concentrated fluid or the amount of plasma that has passed through the plasma outlet line.

8. The fluid separation system of claim 7, wherein the controller is programmed to determine the amount of plasma in said at least a portion of the concentrated fluid based at least in part on the hematocrit of said at least a portion of the concentrated fluid.

9. The fluid separation system of claim 1, further comprising a concentrated fluid weigh scale, wherein the controller is programmed to determine the amount of free plasma hemoglobin in said at least a portion of the concentrated fluid based at least in part on the weight of said at least a portion of the concentrated fluid.

10. The fluid separation system of claim 1, wherein the controller includes a pre-programmed reference equation having one or more constants and representing an experimentally determined relationship between an output of the optical sensor assembly and free plasma hemoglobin concentration and is further programmed to, during a calibration test,
   generate an equation having one or more constants and representing the actual relationship between the output of the optical sensor assembly and free plasma hemoglobin concentration,
   compare at least one of the one or more constants of the reference equation to the corresponding constant or constants of the generated equation,
   register the optical sensor assembly as having passed the calibration test if the differences between the at least one of the one or more constants of the generated equation are less than a predetermined tolerance away from the corresponding constant or constants of the reference equation, and
   register the optical sensor assembly as having failed the calibration test if the differences between the at least one of the one or more constants of the generated equation are greater than a predetermined tolerance away from the corresponding constant or constants of the reference equation.

11. A method of calculating the amount of free plasma hemoglobin in a concentrated fluid separated from a plasma-containing fluid, comprising:
   separating a plasma-containing fluid into separated plasma and a concentrated fluid;
   optically monitoring at least a portion of the separated plasma;
   generating an output indicative of the concentration of free plasma hemoglobin in said at least a portion of the separated plasma;
   calculating the amount of free plasma hemoglobin in at least a portion of the concentrated fluid based at least in part on said output;
   operating a pump to deliver at least a portion of the concentrated fluid to a fluid recipient; and
   generating an alarm or alert signal when the amount of free plasma hemoglobin in the concentrated fluid delivered to and/or to be delivered to the fluid recipient meets or exceeds a preselected or predetermined value.

12. The method of claim 11, further comprising determining a flow rate of a portion of the separated plasma during a period of time and calculating the amount of free plasma hemoglobin in said portion of the separated plasma during said period of time by multiplying the concentration of free plasma hemoglobin in said portion of the separated plasma by the amount of said portion of the separated plasma.

13. The method of claim 12, further comprising calculating the total amount of free plasma hemoglobin in the separated plasma by calculating the amount of free plasma hemoglobin in a portion of the separated plasma during a plurality of consecutive periods of time and adding together said amounts of free plasma hemoglobin in said portions of the separated plasma during said plurality of consecutive periods of time.

14. The method of claim 11, further comprising determining the change in weight of the separated plasma during a period of time to determine the amount of plasma that has been separated out of the plasma-containing fluid during said period of time and calculating the amount of free plasma hemoglobin in the plasma that has been separated out of the plasma-containing fluid during said period of time by multiplying the concentration of free plasma hemoglobin in the plasma that has been separated out of the plasma-containing fluid during said time period by the amount of the plasma that has been separated out of the plasma-containing fluid during said period of time.

15. The method of claim 14, further comprising calculating the total amount of free plasma hemoglobin in the separated plasma by calculating the amount of free plasma hemoglobin in the amount of plasma that has been separated out of the plasma-containing fluid during a plurality of consecutive periods of time and adding together said amounts of free plasma hemoglobin in said amounts of plasma that have been separated out of the plasma-containing fluid during said plurality of consecutive periods of time.

16. The method of claim 11, wherein said calculating the amount of free plasma hemoglobin in said at least a portion of the concentrated fluid includes calculating the amount of free plasma hemoglobin in the separated plasma and multiplying said amount of free plasma hemoglobin in the separated plasma by a ratio factor.

17. The method of claim 11, wherein said calculating the amount of free plasma hemoglobin in said at least a portion of the concentrated fluid includes multiplying the concentration of free plasma hemoglobin in the separated plasma by a ratio factor and by the amount of plasma in said at least a portion of the concentrated fluid.

18. The method of claim 17, wherein the amount of plasma in said at least a portion of the concentrated fluid is determined based at least in part on the hematocrit of said at least a portion of the concentrated fluid.

19. The method of claim 11, wherein said calculating the amount of free plasma hemoglobin in said at least a portion of the concentrated fluid includes determining the weight of said at least a portion of the concentrated fluid.

20. A fluid separation system for separating a plasma-containing fluid into separated plasma and a concentrated fluid, the fluid separation system being configured to cooperate with a fluid flow circuit including a fluid separation chamber and a plasma outlet line associated with the fluid separation chamber for removing separated plasma from the fluid separation chamber, the fluid separation system comprising:
   an optical sensor assembly configured to monitor the contents of the plasma outlet line and produce an output indicative of the concentration of free plasma hemoglobin in the plasma outlet line; and
   a controller programmed to calculate the free plasma hemoglobin concentration of the contents of the plasma outlet line based at least in part on the output of the optical sensor assembly, wherein the controller includes a pre-programmed reference equation having one or more constants and representing an experimentally determined relationship between the output of the optical sensor assembly and free plasma hemoglobin concentration and is further programmed to, during a calibration test, generate an equation having one or more constants and representing the actual relationship between the output of the optical sensor assembly and free plasma hemoglobin concentration, compare at least one of the one or more constants of the pre-programmed reference equation to the corresponding constant or constants of the generated equation, register the optical sensor assembly as having passed the calibration test if the differences between the at least one of the one or more constants of the generated equation are less than a predetermined tolerance away from the corresponding constant or constants of the pre-programmed reference equation, and register the optical sensor assembly as having failed the calibration test if the differences between the at least one of the one or more constants of the generated equation are greater than a predetermined tolerance away from the corresponding constant or constants of the pre-programmed reference equation.

21. The fluid separation system of claim 20, wherein the controller is programmed to compare all of the constants of the pre-programmed reference equation to the corresponding constants of the pre-programmed reference equation and register the optical sensor assembly as having passed the calibration test only if the differences between each constant of the generated equation are less than a predetermined tolerance away from the corresponding constant of the pre-programmed reference equation.

22. A method of calibrating an optical sensor assembly configured to monitor a fluid for the presence of free plasma hemoglobin, comprising:
  providing at least one fluid having a known free plasma hemoglobin concentration or at least one material having optical properties that are generally representative of the optical properties of a corresponding fluid having a known free plasma hemoglobin concentration;
  optically monitoring the at least one fluid or material using the optical sensor assembly;
  generating an output from the optical sensor assembly, with the output being indicative of the concentration of free plasma hemoglobin in the at least one fluid or said corresponding fluid;
  generating an equation using the output from the optical sensor assembly, with the equation having one or more constants and representing the actual relationship between the output of the optical sensor assembly and the concentration of free plasma hemoglobin in the at least one fluid or said corresponding fluid;
  comparing at least one of the one or more constants of the generated equation to the corresponding constant or constants of a reference equation having one or more constants and representing an experimentally determined relationship between the output of the optical sensor assembly and free plasma hemoglobin concentration;
  registering the optical sensor assembly as having passed the calibration test if the differences between the at least one of the one or more constants of the generated equation are less than a predetermined tolerance away from the corresponding constant or constants of the reference equation; and
  registering the optical sensor assembly as having failed the calibration test if the differences between the at least one of the one or more constants of the generated equation are greater than a predetermined tolerance away from the corresponding constant or constants of the reference equation.

23. The method of claim 22, wherein
said comparing at least one of the one or more constants of the generated equation to the corresponding constant or constants of a reference equation includes comparing all of the constants of the reference equation to the corresponding constants of the reference equation and
said registering the optical sensor assembly as having passed the calibration test includes registering the optical sensor assembly as having passed the calibration test only if the differences between each constant of the generated equation are less than a predetermined tolerance away from the corresponding constant of the reference equation.

24. The method of claim 22, wherein
said providing at least one fluid or material includes providing exactly two fluids having different, known free plasma hemoglobin concentrations or providing exactly two materials having optical properties that are generally representative of the optical properties of exactly two corresponding fluids having different, known free plasma hemoglobin concentrations,
said optically monitoring the at least one fluid or material using the optical sensor assembly includes optically monitoring the two fluids or materials using the optical sensor assembly,
said generating an output from the optical sensor assembly includes generating an output for each of the two fluids or materials, and
said generating an equation using the output from the optical sensor assembly includes generating an equation using the two outputs from the optical sensor assembly.

* * * * *